(12) United States Patent
Krishnakumar et al.

(10) Patent No.: US 9,433,378 B2
(45) Date of Patent: Sep. 6, 2016

(54) MODULAR PROCESSING OF MAGNETIC RESONANCE DATA

(71) Applicant: KONINKLIJKE PHILIPS N.V., Eindhoven (NL)

(72) Inventors: Ashwin Krishnakumar, Bangalore (IN); Vinay Parthan, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/074,189

(22) Filed: Mar. 18, 2016

(65) Prior Publication Data

US 2016/0198997 A1    Jul. 14, 2016

Related U.S. Application Data

(63) Continuation of application No. 14/243,018, filed on Apr. 2, 2014, now Pat. No. 9,320,918.

(60) Provisional application No. 61/807,794, filed on Apr. 3, 2013.

(51) Int. Cl.
  *A61B 5/055*  (2006.01)
  *A61B 5/00*   (2006.01)
  *A61N 7/00*   (2006.01)
  *G01R 33/54*  (2006.01)

(52) U.S. Cl.
  CPC ........... *A61B 5/4836* (2013.01); *A61N 7/00* (2013.01); *G01R 33/546* (2013.01)

(58) Field of Classification Search
  CPC .......... A61B 2019/5236; A61B 5/015; A61B 5/055; A61N 2005/1055; A61N 5/1049; A61N 5/1084; A61N 7/02; G01R 33/546
  See application file for complete search history.

(56) References Cited

U.S. PATENT DOCUMENTS

| | | | |
|---|---|---|---|
| 5,291,401 A | 3/1994 | Robinson |
| 6,348,793 B1 | 2/2002 | Balloni |
| 6,963,673 B1 | 11/2005 | Patel |
| 7,106,479 B2 | 9/2006 | Roy |
| 7,189,205 B2 | 3/2007 | McMorrow |
| 8,145,503 B2 | 3/2012 | Backhaus |
| 2005/0018929 A1 | 1/2005 | Lippincott |
| 2009/0209843 A1 | 8/2009 | Graf |

*Primary Examiner* — Mark Remaly

(57) ABSTRACT

The invention provides for medical instrument comprising a magnetic resonance imaging system. Execution of the instruction cause a processor controlling the instrument to: execute a magnetic resonance data processing application thereby providing a plug-in framework, execute a protocol definition interface to load a first selection of the plug-ins into the plug-in framework, acquire the magnetic resonance data by using the pulse sequence data to control the magnetic resonance imaging system; and reconstruct a magnetic resonance image from the magnetic resonance data using the first selection of the plug-ins.

4 Claims, 12 Drawing Sheets

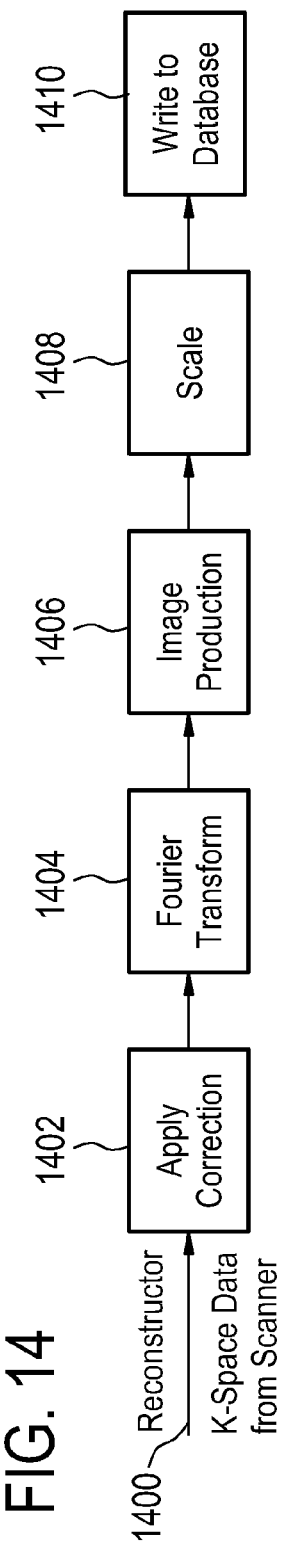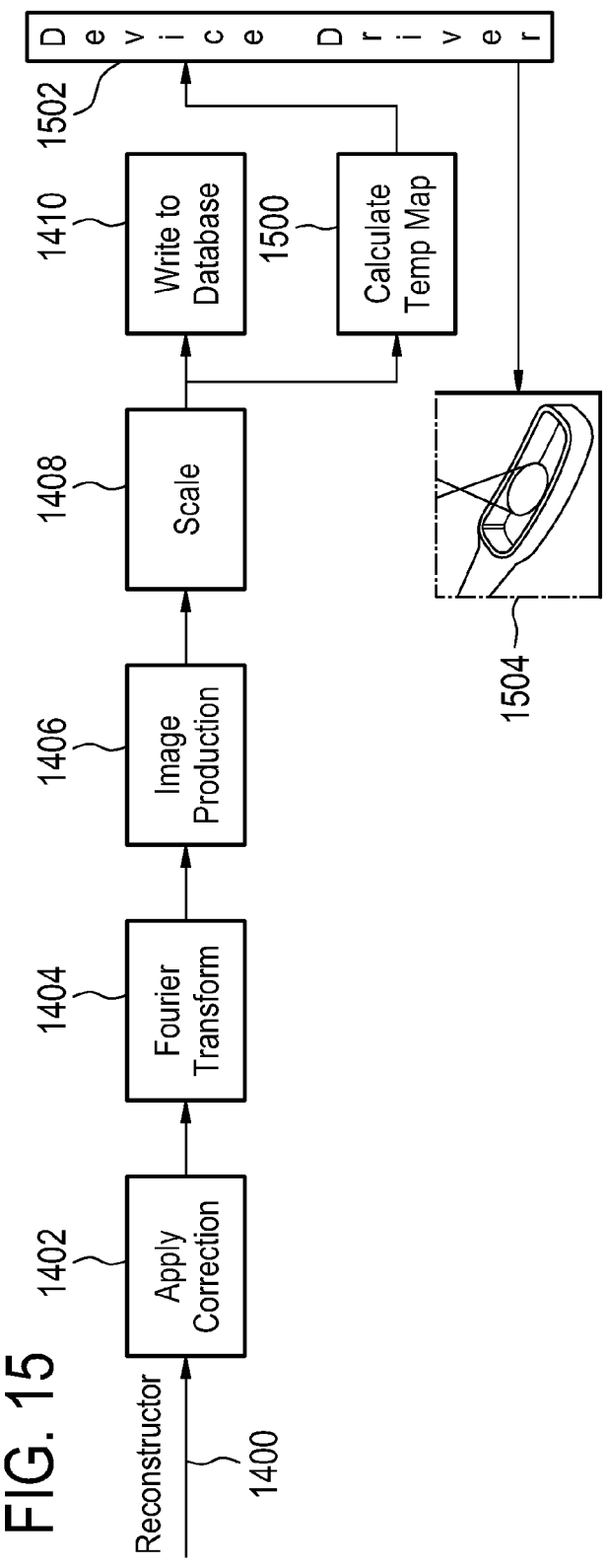

MODULAR PROCESSING OF MAGNETIC RESONANCE DATA

TECHNICAL FIELD

The invention relates to magnetic resonance imaging, in particular to the reconstruction of magnetic resonance images and to magnetic resonance imaging guided therapy.

BACKGROUND OF THE INVENTION

The Magnetic Resonance (MR) Scanner is typically connected to a computer or workstation, which is used to obtain process and store image data which can be processed and displayed as images. The image data is captured as raw data (k-space data or magnetic resonance data) that contains artifacts inherent to the scanner.

During MR reconstruction (when the patient is in the scan room), the raw image data (k-space data) undergoes a set of transformations to convert the images in k-space to image space (spatial domain) before they are displayed on a monitor. The medical professional then reviews the images for a patient or saves the images and recalls them later for more diagnosis.

Image processing algorithms are applied to the raw image data to convert them from k-space to image space so that it can be viewed, analyzed and diagnosed by the medical professional. There are many image processing algorithms that add diagnostic value to these images. Image processing is a research field in itself, with many algorithms of high diagnostic value being continually developed. New image processing algorithms are often developed and integrated into the reconstruction chain.

The image processing steps that needs to be applied depends on the scan type (like Spin Echo scan, Gradient Echo scan, SENSE scan, Dixon scan etc). Currently as the scan time of MR scanner is considerably high there is continuous research going on to come up with new scan type which would reduce the scan time. Often whenever a new scan type is introduced it would warrant for a new image processing algorithm in reconstruction chain.

For fast execution of image reconstruction the computer resources like the CPU (cores), memory will have to be used judiciously and efficiently.

Currently MR image reconstruction is developed as a monolithic and closed package in a programming language like C++ without the clear separation of mathematical numerical processing and software engineering disciplines. This application is compiled for distribution to customers who purchase, lease or own the MR Scanner. Integration of new algorithms requires recompiling the application software. Also the number of threads to be used by the application is hardcoded in the application. The off-the-shelf libraries used are hardcoded in the code and any change in the library needs code modification and recompilation of the application software.

United States patent application US 2005/0018929 A1 discloses a method for dynamically editing and enhancing image-processing chains in medical imaging equipment.

SUMMARY OF THE INVENTION

The invention provides for a medical instrument, a computer program product and a method in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer. Magnetic resonance data can also be referred to as k-space data.

Magnetic Resonance (MR) thermometry data is defined herein as being the recorded measurements of radio frequency signals emitted by atomic spins by the antenna of a Magnetic resonance apparatus during a magnetic resonance imaging scan which contains information which may be used for magnetic resonance thermometry. Magnetic resonance thermometry functions by measuring changes in temperature sensitive parameters. Examples of parameters that may be measured during magnetic resonance thermometry are: the proton resonance frequency shift, the diffusion coefficient, or changes in the T1 and/or T2 relaxation time may be used to measure the temperature using magnetic resonance. The proton resonance frequency shift is temperature dependent, because the magnetic field that individual protons, hydrogen atoms, experience depends upon the surrounding molecular structure. An increase in temperature decreases molecular screening due to the temperature affecting the hydrogen bonds. This leads to a temperature dependence of the proton resonant frequency.

An 'ultrasound window' as used herein encompasses a window which is able to transmit ultrasonic waves or energy. Typically a thin film or membrane is used as an ultrasound window. The ultrasound window may for example be made of a thin membrane of BoPET (Biaxially-oriented polyethylene terephthalate).

In one aspect the invention provides for a medical instrument comprising a magnetic resonance imaging system for acquiring magnetic resonance data from an imaging zone. The medical instrument further comprises a memory containing machine-executable instructions, a magnetic resonance data processing application, pulse sequence data, at least one numerical algorithm library, a plug-in wrapper library configured for providing the at least one numerical algorithm library as plug-ins, and a protocol definition interface. The magnetic resonance data processing application is an application which enables the processor to process or reconstruct magnetic resonance data and turn it into other forms such as a magnetic resonance image. The protocol definition interface is an executable program which is configured for controlling the loading of plug-ins and the execution order of the plug-ins. A numerical algorithm library as used herein encompasses executable computer code for providing implementations of one or more numerical algorithms. The plug-in wrapper library is software which is used for providing an algorithm or function in the at least one numerical algorithm library as a plug-in to make it available to the magnetic resonance data processing application.

The medical instrument further comprises at least one processor for controlling the medical instrument. Execution of the instructions causes the processor to execute the magnetic resonance data processing application thereby providing a plug-in framework. A plug-in as used herein encompasses a software component which may be used to add a specific feature or to extend another software application. In this example the magnetic resonance data processing application is extended by the use of plug-ins. The plug-in framework from the magnetic resonance data processing application provides a framework or interface for plug-ins used to provide the extension to the magnetic resonance data processing application.

Execution of the instructions further causes the at least one processor to execute the protocol definition interface to load a first selection of the plug-ins into the plug-in framework. For example for a particular magnetic resonance protocol one may desire a certain combination of image processing or data manipulation plug-ins. The protocol definition interface loads a first selection of the plug-ins into the plug-in framework. Execution of the instructions cause the at least one processor to further acquire the magnetic resonance data by using the pulse sequence data to control the magnetic resonance imaging system. Pulse sequence data as used herein encompasses commands that the processor can use or data which may be transformed into commands for controlling the magnetic resonance imaging system to acquire the magnetic resonance data. Execution of the instructions further cause the at least one processor to reconstruct a magnetic resonance image from the magnetic resonance data using the first selection of the plug-ins. In this example the post-processing of the magnetic resonance data was performed using the plug-ins. This may enable a more flexible means of updating or modifying the functionality of the magnetic resonance imaging system.

A drawback of current approach for image processing chains or k-space data processing chains in medical imaging systems includes:

a. The image processing developers in MR are generally domain experts like physicists who are not well versed with software engineering concepts like threading, task based programming, memory management etc., and hence are not able to efficiently develop new algorithms.

b. As the image processing chains are done thread based programming (with number of threads predetermined) and not task based approach the application doesn't scale with the hardware.

c. It may not be possible to take advantage of the GPU processing power.

d. To update the current image processing chains it may be necessary to update and reinstall the imaging application software to add even a single new image processing algorithm. Another technical problem arises in integrating new image data processing algorithms, because these are often developed by third parties at different geographical location.

Examples may provide a means for solving one or more the above mentioned problems.

In another embodiment the medical instrument further comprises a treatment system for directing energy at a target zone within the imaging zone. The energy may for instance be acoustic energy or it may be heat, or it may be ionizing radiation from, for example a gamma or X-ray source. Execution of the instructions further cause the processor to receive treatment plan data descriptive of commands for controlling the treatment system to direct energy at the target zone. Execution of the instructions further cause the protocol definition interface to further load a second selection of the plug-ins operable for generating treatment system control commands using the magnetic resonance image and the treatment plan data.

The second selection of plug-ins are used as part of a control system for the treatment system. Execution of the instructions further cause the processor to repeatedly acquire the magnetic resonance data and reconstruct the magnetic resonance image using the first selection of the plug-ins. That is to say the magnetic resonance data is repeatedly acquired and the image is repeatedly reconstructed from the acquired data. Next execution of the instructions further cause the at least one processor to repeatedly generate the treatment system control commands using the second selection of the plug-ins.

Execution of the instructions further cause the processor to repeatedly control the treatment system using the treatment system control commands. The second selections of the plug-ins are used to process the magnetic resonance image and the treatment plan data to directly generate commands for controlling the treatment system. In this example the first selection of the plug-ins and the second selection of the plug-ins are used in a control loop for controlling the treatment system in response to the repeatedly acquired magnetic resonance data. The use of the plug-ins provides for a more flexible and extensible system for the control of the treatment system.

In another embodiment the treatment system is a high-intensity focused ultrasound system.

In another embodiment the magnetic resonance imaging image comprises a temperature map. The temperature map may for instance be used for measuring the heating of the subject by the high-intensity focused ultrasound system in real time and then uses as feedback for generating the treatment control commands. This may result in more accurate heating of the target zone by the high-intensity focused ultrasound system.

In another embodiment the treatment system is an external beam radiotherapy system for irradiating the target zone with a beam of ionizing radiation. The magnetic resonance image for instance could be used for tracking the external and/or internal motion of the subject. The magnetic resonance images acquired could therefore be used to more accurately target the target zone with the beam of ionizing radiation.

In another embodiment the external beam radiotherapy system is a gamma knife.

In another example the external beam radiotherapy system is a LINAC.

In another embodiment the external beam radiotherapy system is an x-ray treatment system.

In another embodiment the external beam radiotherapy system is a charged particle accelerator.

In another embodiment the at least one processor is two or more processors operable for executing multiple processor threads. Execution of the instructions causes the processor to execute the plug-ins using the multiple processor threads.

In another embodiment the medical instrument further comprises at least one graphics processor. The magnetic resonance data processing application is configured for executing at least a portion of the plug-ins using at least one graphics processor.

In another embodiment the at least one numerical algorithm library is at least two numerical algorithm libraries. Each of the at least two numerical algorithm libraries is implemented in a different programming language.

In another embodiment the protocol definition interface is configured for controlling the loading of the plug-ins and the execution order of the plug-ins using a script. For instance the protocol definition interface could refer to or have commands executed by the script which cause the plug-ins to be loaded into the plug-in framework.

In another embodiment the pulse sequence data comprises additional data such as the script for controlling the protocol definition interface. In other examples the inclusion of the pulse sequence data of the script is by having a logical link in the pulse sequence data which points or identifies the proper script.

Having the pulse sequence data somehow access the script may be beneficial because it enables the proper pulse sequence to be linked or access the appropriate plug-ins for processing the data.

In another aspect the invention provides for a computer program product comprising machine-executable instructions for execution by at least one processor controlling the medical instrument. The medical instrument comprises a magnetic resonance imaging system for acquiring magnetic resonance data from an imaging zone. The medical instrument further comprises a memory containing; a magnetic resonance data processing application, pulse sequence data, at least one numerical algorithm library, a plug-in wrapper library configured for providing the at least one numerical algorithm library as plug-ins, and a protocol definition interface.

The at least one numerical algorithm library comprises machine-executable code for performing at least one numerical algorithm. The magnetic resonance data processing application is configured for implementing a plug-in framework for a numerical processing of the magnetic resonance data. The protocol definition interface is configured for controlling the loading of the plug-ins and the execution order of the plug-ins. Execution of the machine-executable instructions cause the at least one processor to execute the magnetic resonance data processing application thereby providing a plug-in framework. Execution of the machine-executable instructions further causes at least one processor to execute the protocol definition interface to load a first selection of the plug-ins into the plug-in framework.

Execution of the machine-executable instructions further causes the at least one processor to acquire the magnetic resonance data by using the pulse sequence data to control the magnetic resonance imaging system. Execution of the machine-executable instructions further cause the at least one processor to reconstruct a magnetic resonance image from the magnetic resonance data using the first selection of the plug-ins.

In another embodiment the medical instrument further comprises a treatment system for directing energy at a target zone within the imaging zone. Execution of the instructions further cause the processor to receive treatment plan data descriptive of commands for controlling the treatment system to direct energy at the target zone. Execution of the protocol definition interface further loads a second selection of the plug-ins operable for generating treatment system control commands using the magnetic resonance image and the treatment plan data. Execution of the machine-executable instructions further cause the at least one processor to repeatedly acquire the magnetic resonance data and reconstruct the magnetic resonance image using the first selection of the plug-ins. Execution of the instructions further cause the at least one processor to repeatedly generate the treatment system control commands using the second selection of the plug-ins. Execution of the instructions further cause the at least one processor to repeatedly control the treatment system using the treatment system control commands.

In another aspect the invention provides for a method of operating the medical instrument comprising the magnetic resonance imaging system for acquiring magnetic resonance data from an imaging zone. The medical instrument further comprises a memory containing: a magnetic resonance data processing application, pulse sequence data, at least one numerical algorithm library, a plug-in wrapper library configured for providing the at least one numerical algorithm library as plug-ins, and a protocol definition interface. The at least one numerical algorithm library comprises machine-executable code for performing at least one numerical algorithm.

The magnetic resonance data processing application is configured for implementing a plug-in framework for numerical processing of the magnetic resonance data. The protocol definition interface is configured for controlling the loading of the plug-ins and the execution order of the plug-ins. The method comprises the step of executing the magnetic resonance data processing application thereby providing a plug-in framework. The method further comprises the step of executing the protocol definition interface to load a first selection of the plug-ins into the plug-in framework. The method further comprises the step of acquiring the magnetic resonance data by using the pulse sequence data to control the magnetic resonance imaging system. The method further comprises the step of reconstructing the magnetic resonance image from the magnetic resonance data using the first selection of the plug-ins.

In another embodiment the medical instrument further comprises a treatment system for directing energy at a target zone within the imaging zone. The method further comprises receiving treatment plan data descriptive of commands for controlling the treatment system to direct energy at the target zone. The method further comprises using the protocol definition interface to further load a second selection of plug-ins operable for generating treatment system control commands using the magnetic resonance image and the treatment plan data. The method further comprises the step of repeatedly acquiring the magnetic resonance data and reconstructing the magnetic resonance image using the selection of the plug-ins. The method further comprises the step of generating the treatment system control commands using the second selection of the plug-ins. The method further comprises the step of repeatedly controlling the treatment system using the treatment system control commands.

Embodiments may provides a method of adding new algorithm/processing step developed in any programming language (like MATLAB) to existing reconstruction chains without the need for recompiling the application software. Embodiments may also provides a method to use and change off-the-shelf mathematical libraries at runtime without the need for recompiling the application software.

Embodiments may allows usage of GPU libraries like NPP, CUDA which would run mathematical/signal processing routines on GPU if available on the system and thus improve the performance of the image processing chain.

Embodiments may enable the separation of mathematical numerical processing and software engineering disciplines and thus enables the fast research/development of new algorithms.

Embodiments may allow the research scientists in radiology field in developing new algorithms in their favorite language and using on the scanner without requiring a recompilation of the application software.

Embodiments may allow scaling the magnetic resonance data processing application with the hardware improvements and hence enable more scans to be performed per day.

Embodiments may allows the medical professional such as radiologist to customize the magnetic resonance data processing application used in the scanner without requiring a software update or reinstallation and without calling the service engineer.

Embodiments may use an interpreted language for linking and sequencing the image processing elements within image-processing chains, so that the chain can be changed dynamically.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which:

FIG. 14 shows a reconstruction graph or the sequence is used to reconstruct a magnetic resonance image for a diagnostic magnetic resonance imaging system;
and
FIG. 15 shows how the sequence of FIG. 14 may be modified for controlling a magnetic resonance imaging system.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
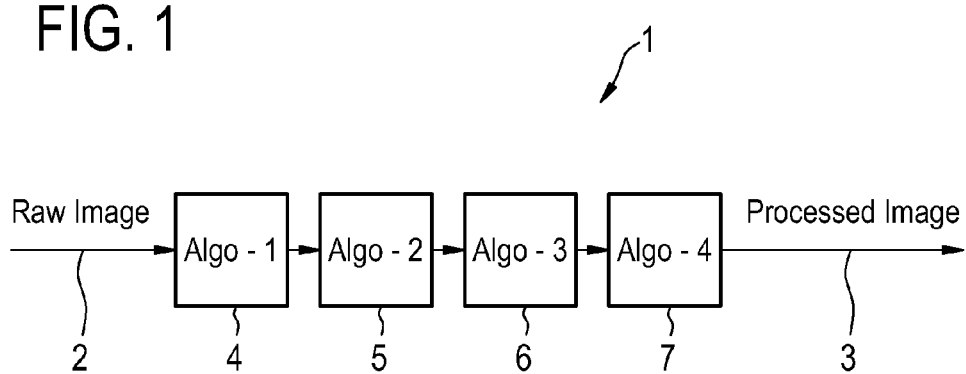
FIG. 1 flow chart illustrating a data processing chain.

FIG. 1 shows an example of an image or data processing chain 1. The image or data processing chain may also be referred to as a reconstructor. A raw image 2 is fed into the chain 1 and a processed image 3 is received at the end of the chain. In this example there are four algorithms 4, 5, 6, 7 shown in the chain. A algorithm used 4, 5, 6, 7 in a chain 1 may be referred to as a node.

As stated above, FIG. 1 illustrates a simple MR image reconstruction chain 1. The blocks 4, 5, 6, 7 in the reconstruction chain 1 are applied to the raw imaging data 2 to produce a processed image 3. These process blocks each include a respective algorithm which is executed when this block of the computer program is executed.

Figure 2:
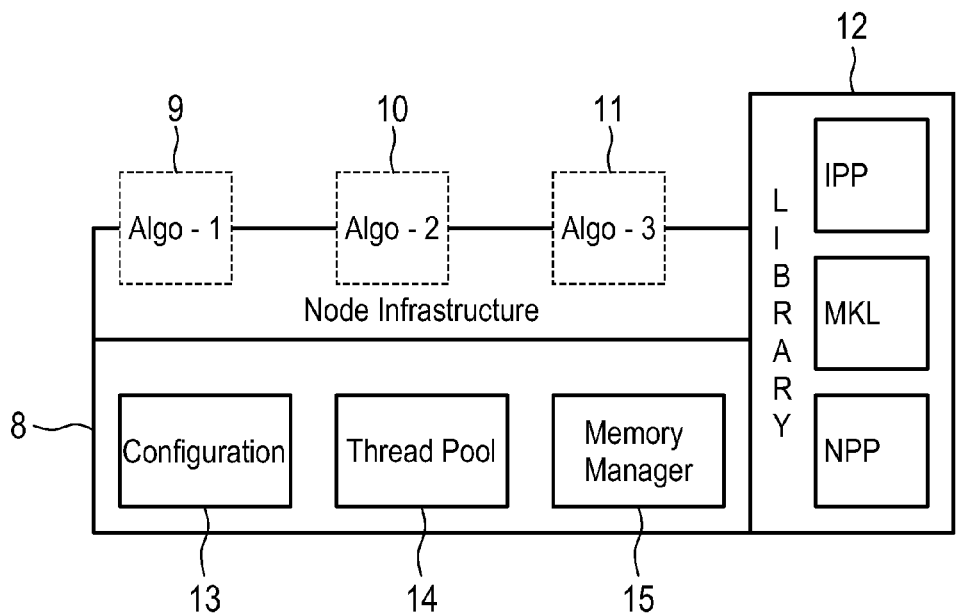
FIG. 2 shows a high level implementation of an image or data processing application.

As seen from FIG. 1 the processed images are generated after applying a sequence of transformations or algorithms (represented as blocks) to the raw image data. These blocks (hereafter referred as "Nodes" in this document) are generic. The invention provides an efficient, flexible and open architecture for execution of the reconstruction chain. FIG. 2 illustrates the high level architecture of the system of FIG. 1. FIG. 2 shows a high level implementation 8 of the magnetic resonance data processing application. The magnetic resonance data processing application is shown as having an implementation of a node infrastructure or plug-in framework. The algorithms 9, 10 and 11 can be seen as interfacing with the plug-in framework. The system also comprises a numerical library 12 which can be used by the algorithms 9, 10, 11. IPP, MKL, and NPP refer to different numerical libraries that are available.

Within the magnetic resonance data processing application there are components for doing the configuration of the algorithms 9, 10, 11, a thread pool management 14, and a memory manager 15.

Here the domain/mathematics and the software engineering concepts are separated. The software engineering part like the threading, memory management, configuration support is handled by the platform 8. The platform 8 also provides the node infrastructure, which is the generic part of all Nodes. The node infrastructure may also be referred to as a plug-in framework and the nodes are implemented as plug-ins.

The Node infrastructure handles the data transfer between nodes, the manipulation of data (e.g. Splitting of data, Transpose of data etc), memory allocation/de-allocation and parallel execution of Nodes. The node infrastructure in-turn uses the Memory manager, Thread pool and the configuration module of the platform.

Library module 12 provides a generic interface for the signal processing/mathematical libraries which the algorithm encapsulated in the Nodes can use. Library module is a wrapper over off-the-shelf, 3rd party libraries like IPP, MKL, APL, NPP etc. Library module provides mechanism to configure the 3rd party library to be used for each mathematical routine. It is possible to extend the Library module to support new 3rd party library without recompiling the application software.

The Library module 12 also provides support for GPU libraries like the NPP, CUDA which enables the signal processing routines like the FFT, Convolution, and Correlation etc to be executed on the Graphics card for enhanced performance if the graphics card is available on the system.

The development effort and the complexity of node development may be greatly reduced because of this architecture.

Figure 3:
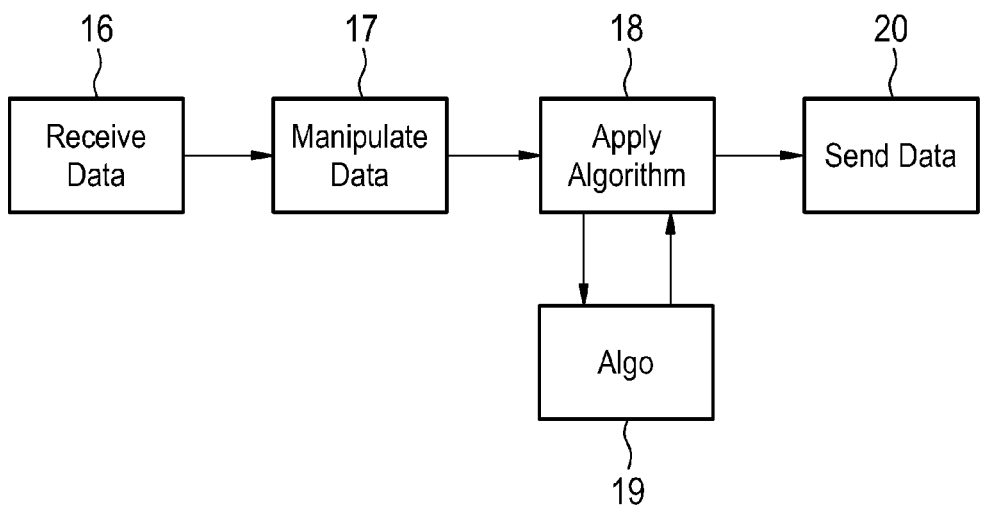
FIG. 3 illustrates various operations performed by plug-ins or nodes.

FIG. 3 illustrates various operations performed by each of the plug-ins or nodes. In step 16 data is received. Next the data is manipulated and applied or transformed into a useful form. Next in step 18 the algorithm is applied and the data is sent to the algorithm 19. After the algorithm has responded the data is returned 20. FIG. 3 illustrates the responsibilities of each node. The generic part of the node includes receiving data from previous node, manipulating the data like splitting the data, transposing the data if required, applying the algorithm and sending the data to the next node [16, 17, 18, 20]. The algorithm [19] that needs to be applied would be different for each node.

Figure 4:
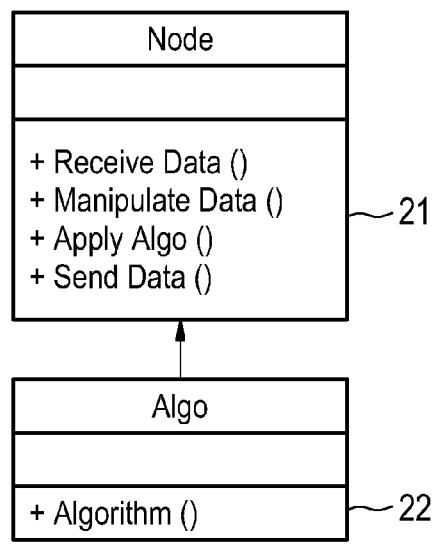
FIG. 4 illustrates a node and shows how it is designed to implement an algorithm.

FIG. 4 illustrates a node 21 and shows how it is designed to implement the algorithm 22. Here the generic part of the node is handled in the base class and the derived class just implements the actual algorithm. Thus the Image processing algorithm developer can concentrate only on the algorithm development and rest will be handled by the base class. The base class is part of the Node infrastructure layer of platform.

Figure 5:
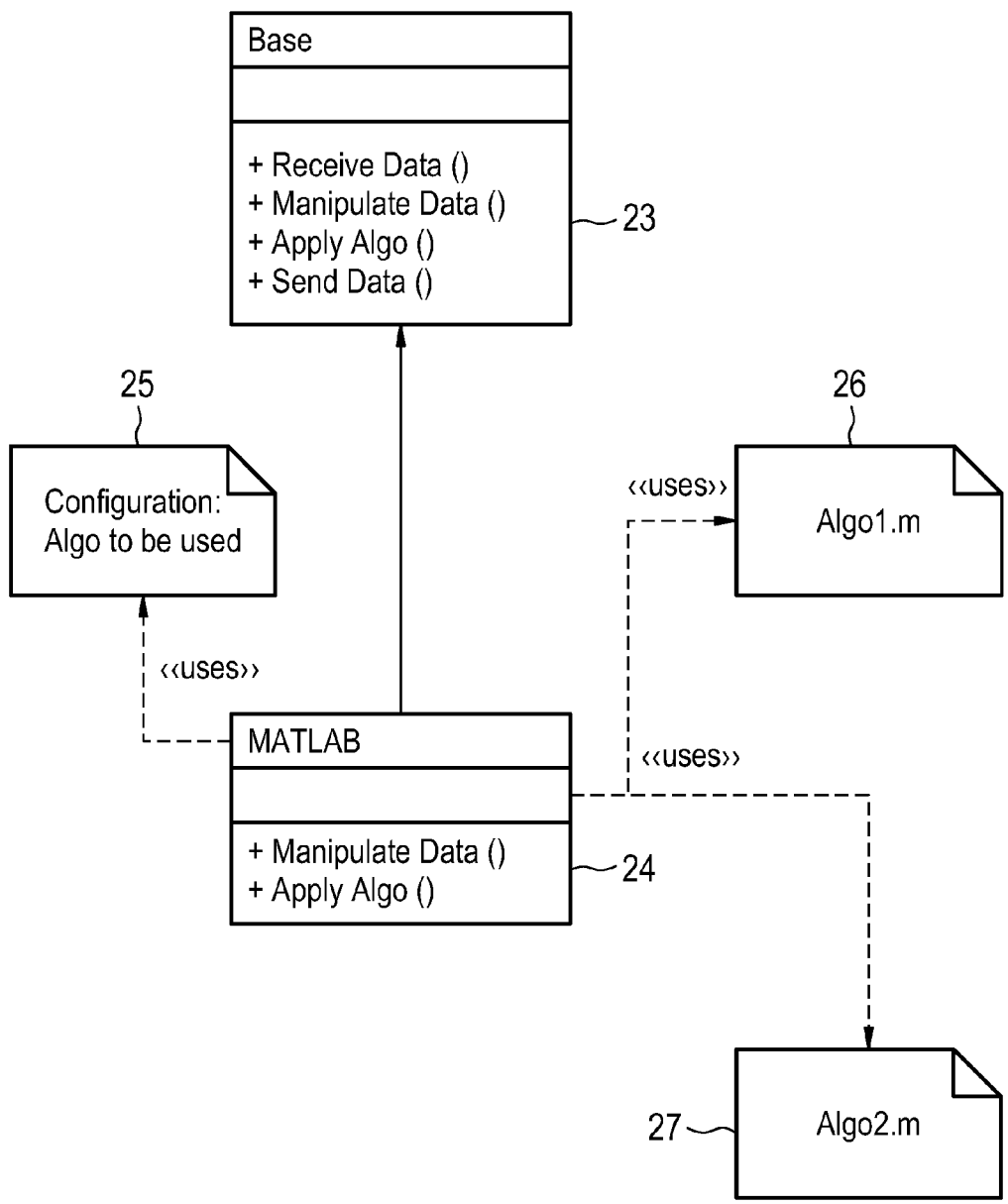
FIG. 5 illustrates how algorithms developed in other languages can be handled.

FIG. 5 illustrates how algorithms developed in other languages like MATLAB can be handled. Here the MATLAB class 24 is a generic class for all algorithms developed in MATLAB. The ManipulateData method of the Node class 23 is overridden to manipulate/convert the data format from C++ to MATLAB. The ApplyAlgo( ) is again overridden to look at the configuration 25 to determine which MATLAB file 26, 27 needs to be executed. The ApplyAlgo( ) also handles the conversion of the processed data from MATLAB format to C++ format. The MATLAB file can be built into binary using MATLAB compiler to avoid availability of MATLAB on the execution system. On similar lines algorithms developed in other languages can be handled.

Figure 6:
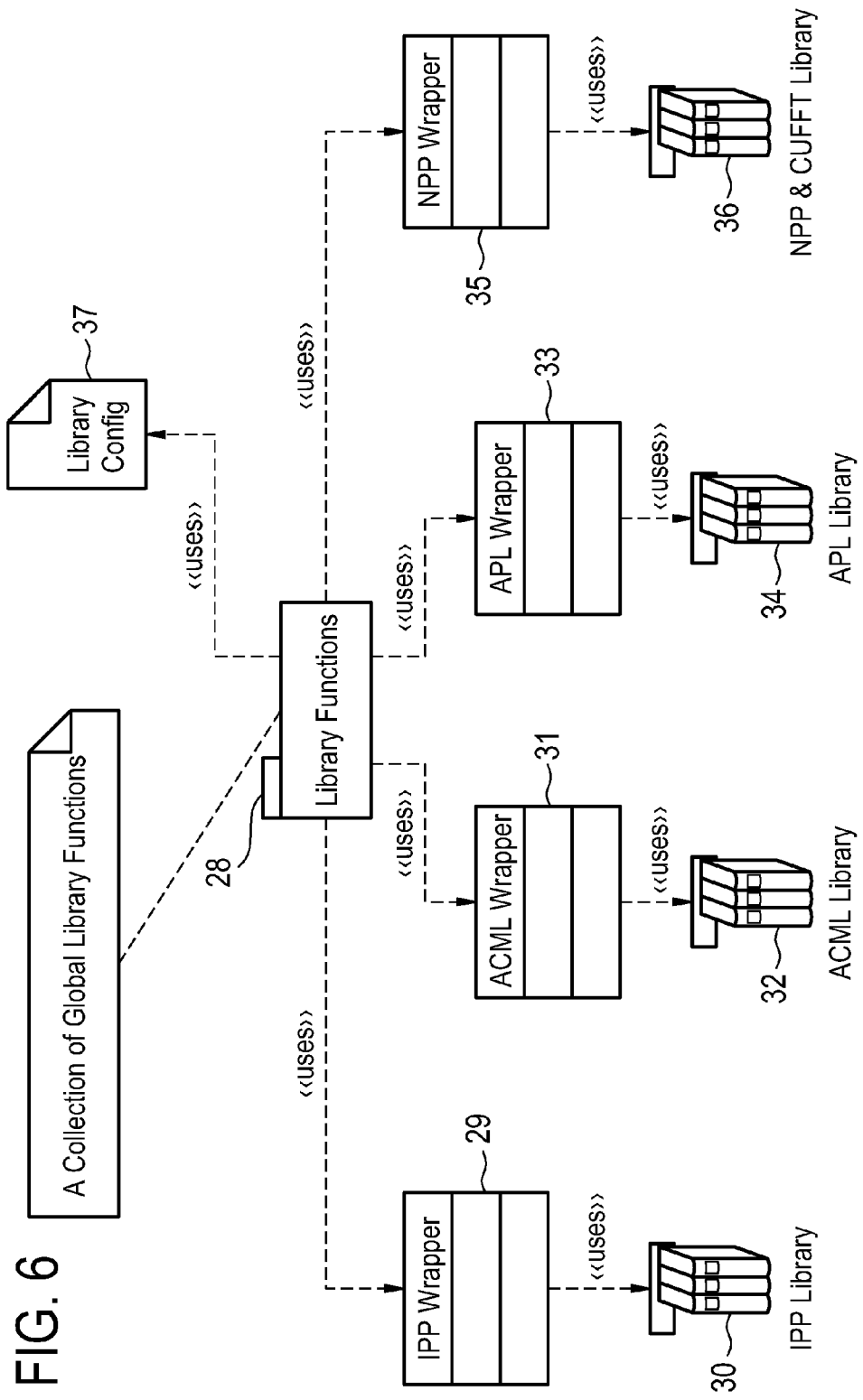
FIG. 6 illustrates the design of a library module.

FIG. 6 illustrates the design of a library module. The library functions 28 are a collection of mathematical/signal/image processing routines supported. The configuration file 37 lists for each of the routine which 3rd party library is to be used. The configuration file is a text based file and any modification here wouldn't require a recompilation of the application. As each of the 3rd party library is provided by different vendors the signature of the same routines is not the same across different library and hence a wrapper is provided for each library. The wrapper 29, 31, 33, 35 acts like an adapter between the generic signature exposed by the library function 28 and the specific libraries 30, 32, 34, 36. It is very difficult to find a single library which provides all the mathematical/signal/image processing routines and all of them being efficient. What is found often is some of the routines are efficient in one 3rd party library and others in other 3rd party library. The above mechanism of configuring which 3rd party library to use of a particular routine allows to use the best 3rd party of library for each routine. It is very easy to extend this to support other libraries, just a development of a wrapper which adapts each routine signature from the generic signature to that expected by the 3rd party library.

Figure 7:
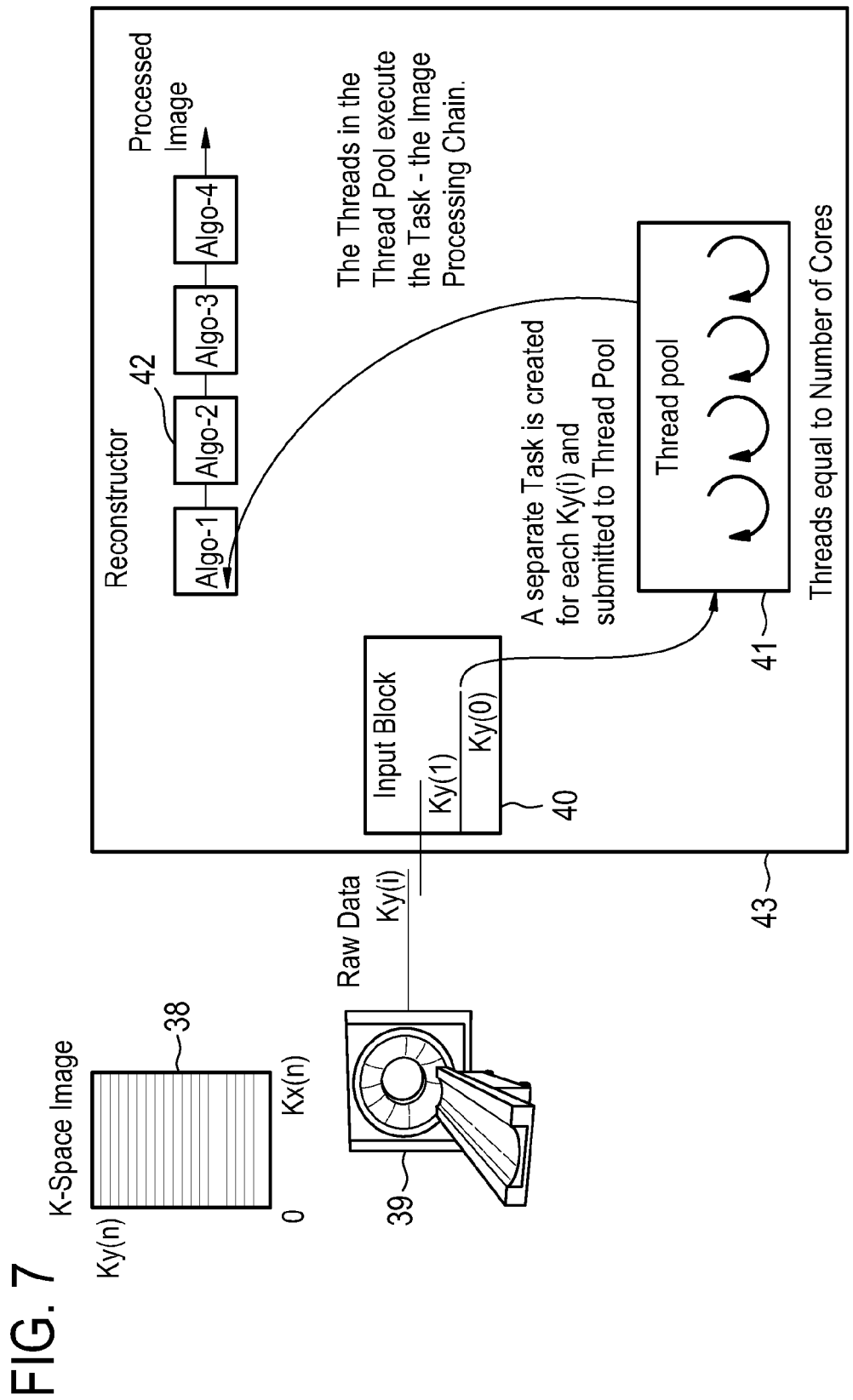
FIG. 7 illustrates the execution of a reconstructor chain using a thread pool on a multi-core processor computer.

FIG. 7 illustrates the execution of the reconstructor chain 42 using the thread pool 41 on a multi-core processor computer. The k-space (raw data) 38 is acquired by the MR scanner 39 each row (Ky) at a time. As the row is acquired, it is sent to the reconstructor 43. An input node 40 is provided which reads the acquired data one row at a time and creates a task for each row. The method set for the task is the first algorithm (Node) in the reconstruction chain 42. The task created is submitted to the thread pool 41. The thread pool creates threads equal to the number of cores on the system. This is done to avoid context switching. The task execution would start from the first node in the reconstruction chain and keep executing the subsequent nodes in the chain. At certain point in the chain it would be required to have the complete k-space data for further processing, a special kind of node which collects all the rows to form a 2d data is to be used in the chain. Once the data is collected this node would again submit a task with the collected 2d data to the thread pool with the next node processing as the task execution method. If the subsequent nodes don't require 2D data to work on they can further split the data and create tasks for each split data and submit the task to the thread pool in the manipulate method( ). This will further parallelize the execution.

Examples may provide for a method for efficiently execution of MR image reconstruction on a multi-core processor with the flexibility of one or more of the following features:

1. Using image processing algorithms developed in multiple languages in a reconstruction chain.

2. Using efficient off-the-shelf 3rd party libraries and changing them at runtime without recompiling the reconstruction program.

3. Possibility of execution of certain mathematical/signal/image processing routines on the graphics card if available on the system without re-compiling the construction program 4. Dynamically controlling the sequence of image processing algorithms without recompiling the reconstruction program.

Figure 8:
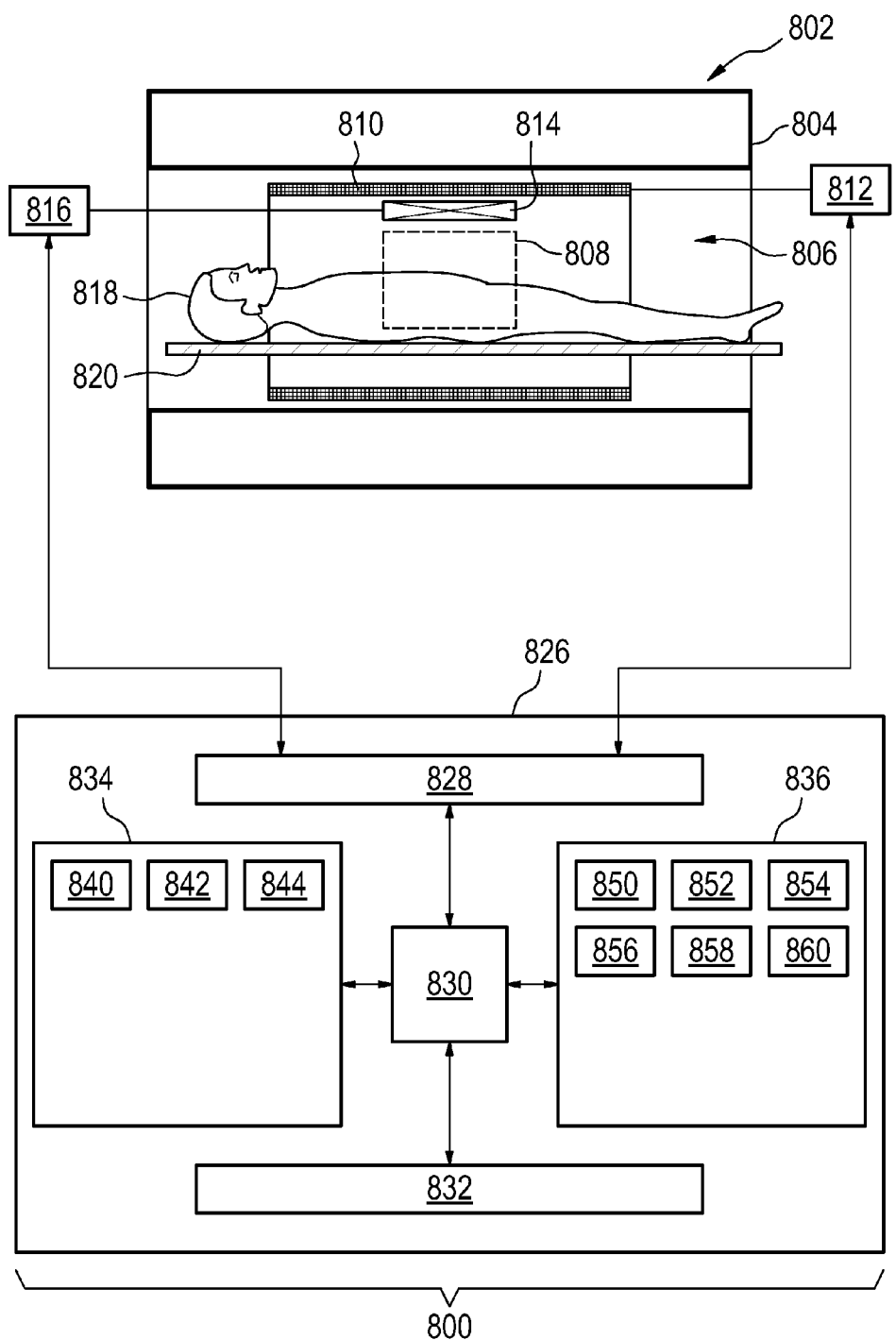
FIG. 8 illustrated an example of a medical instrument.

FIG. 8 illustrates an example of a medical instrument 800. The medical instrument 800 comprises magnetic resonance imaging system 802 with a magnet 804. The magnet 804 is a superconducting cylindrical type magnet 804 with a bore 806 through it. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 806 of the cylindrical magnet 804 there is an imaging zone 808 where the magnetic field is strong and uniform enough to perform magnetic resonance imaging.

Within the bore 806 of the magnet there is also a set of magnetic field gradient coils 810 which is used for acquisition of magnetic resonance data to spatially encode magnetic spins within the imaging zone 808 of the magnet 804. The magnetic field gradient coils 810 connected to a magnetic field gradient coil power supply 812. The magnetic field gradient coils 810 are intended to be representative. Typically magnetic field gradient coils 810 contain three separate sets of coils for spatially encoding in three orthogonal spatial directions. A magnetic field gradient power supply supplies current to the magnetic field gradient coils. The current supplied to the magnetic field gradient coils 810 is controlled as a function of time and may be ramped or pulsed.

Adjacent to the imaging zone 808 is a radio-frequency coil 814 for manipulating the orientations of magnetic spins within the imaging zone 808 and for receiving radio transmissions from spins also within the imaging zone 808. The radio frequency antenna may contain multiple coil elements. The radio frequency antenna may also be referred to as a channel or antenna. The radio-frequency coil 814 is connected to a radio frequency transceiver 816. The radio-frequency coil 814 and radio frequency transceiver 816 may be replaced by separate transmit and receive coils and a separate transmitter and receiver. It is understood that the radio-frequency coil 814 and the radio frequency transceiver 816 are representative. The radio-frequency coil 814 is intended to also represent a dedicated transmit antenna and a dedicated receive antenna. Likewise the transceiver 816 may also represent a separate transmitter and receivers. The radio-frequency coil 814 may also have multiple receive/transmit elements and the radio frequency transceiver 816 may have multiple receive/transmit channels.

The magnetic field gradient coil power supply 812 and the transceiver 816 are connected to a hardware interface 828 of computer system 826. The computer system 826 further comprises a processor 830. The processor 830 is connected to the hardware interface 828, a user interface 832, computer storage 834, and computer memory 836. The contents of the computer storage 824 and the computer memory 836 may duplicate each other or elements shown in one may be alternatively located in the other.

The computer storage 834 is shown as containing pulse sequence data 840. The computer storage 834 is further shown as containing magnetic resonance data 842. The computer storage 834 is further shown as containing a magnetic resonance image 844.

The computer memory 836 is shown as containing a control module 850. The control module 850 contains computer-executable code which enables the processor 830 to control the operation and function of the medical instrument 800. For instance the control module 850 may use the pulse sequence data 840 to acquire the magnetic resonance data 842. The computer memory 836 is further shown as containing a magnetic resonance data processing application 852. The magnetic resonance data processing application 852 uses plug-ins to reconstruct the magnetic resonance image 844 from the magnetic resonance data 842. The computer memory 836 is further shown as containing a numerical library 854 which contains at least one library of numerical algorithms and each library implements at least one numerical algorithm.

The computer memory 836 is further shown as containing a plug-in wrapper library 856. The plug-in wrapper library 856 provides a wrapper for each of the algorithms in the numerical library 854 so they can be implemented as plug-ins. The computer memory 836 is further shown as containing a plug-in wrapper library 856. The first selection of plug-ins 858 is a selection of plug-ins implemented by the plug-in wrapper library 856. The computer memory 836 is further shown as containing a protocol definition interface 860 which controls the loading of the first selection of plug-ins 858 into the magnetic resonance data processing application 852.

Figure 9:
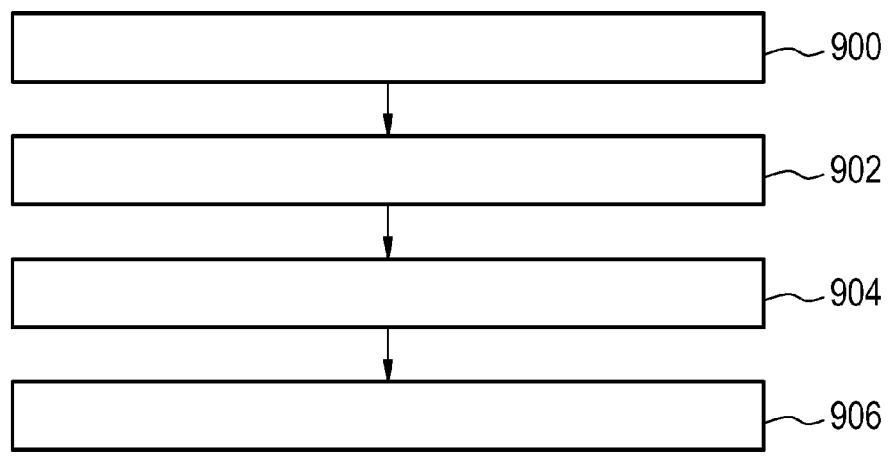
FIG. 9 shows a block diagram which illustrates a method of operating the medical instrument of FIG. 8.

FIG. 9 shows a flowchart which illustrates a method of operating the medical instrument 800 of FIG. 8. First in step 900 the magnetic resonance data processing application 852 is executed thereby providing a plug-in framework. Next in step 902 the protocol definition interface 860 is executed to load a first selection of the plug-ins 858 into the plug-in framework. Next in step 904 the magnetic resonance data 842 is acquired by using the pulse sequence data 840 to control the magnetic resonance imaging system 802. Finally in step 906 the magnetic resonance image 844 is reconstructed from the magnetic resonance data 842 using the first selection of the plug-ins 858.

Figure 10:
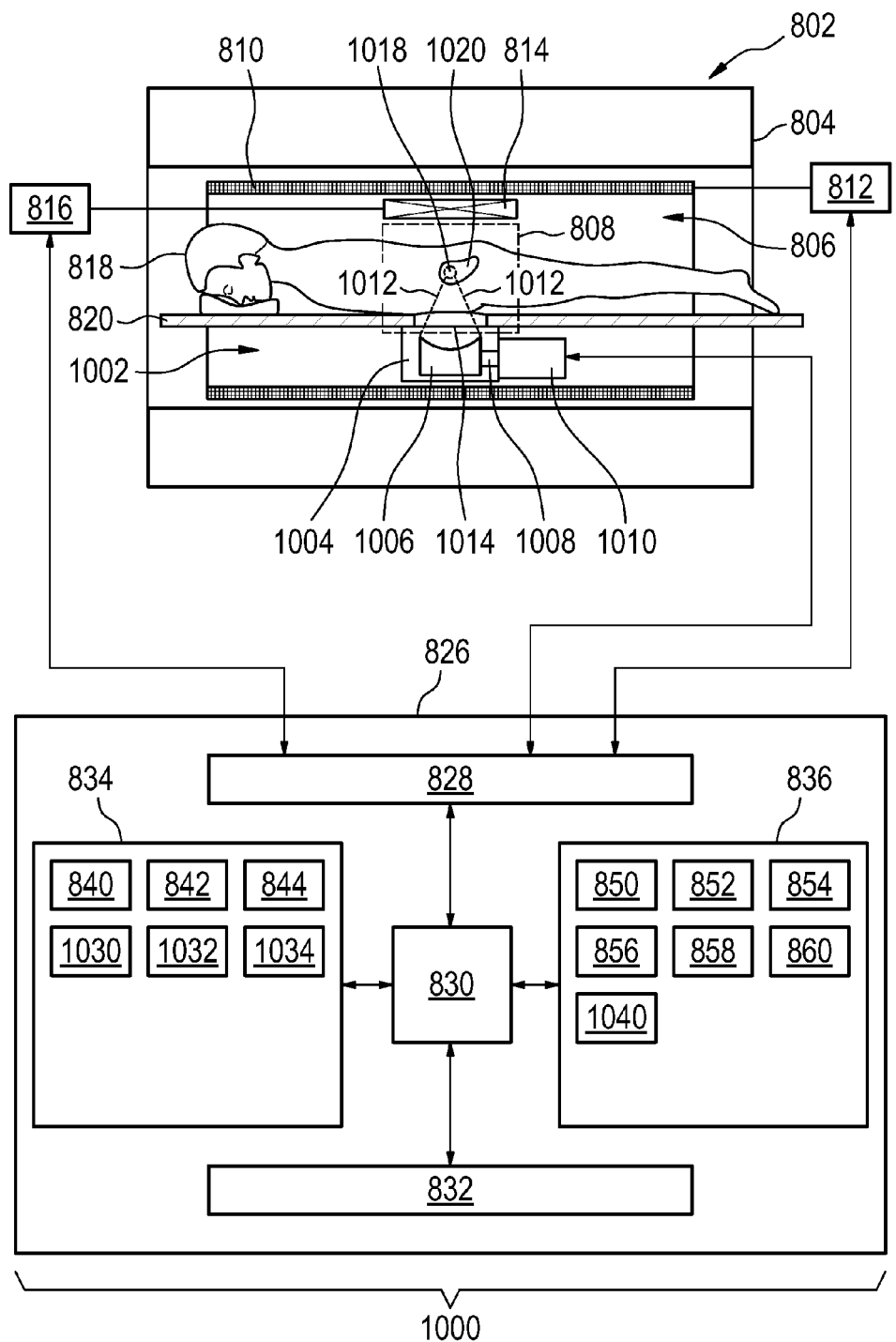
FIG. 10 illustrates a further example of a medical instrument.

FIG. 10 shows a further example of a medical instrument 1000. The medical instrument 1000 is similar to that shown in FIG. 8 except the medical instrument further comprises an additional high-intensity focused ultrasound system 1002. The high-intensity focused ultrasound system 1002 is intended to be representative. The high-intensity focused ultrasound system could also be for example replaced with a gamma knife, a LINAC, an x-ray treatment system, a charged particle accelerator, or other type of external beam radiotherapy system.

The high-intensity focused ultrasound system 1002 comprises a fluid-filled chamber 1004 which houses an ultrasound transducer 1006. The ultrasound transducer 1006 is mechanically positioned by a mechanical positioning system 1008. There is an actuator 1010 for actuating the mechanical positioning system. In alternative embodiments the ultrasound transducer may be a manually positioned external transducer without the fluid-filled chamber 1004 or mechanical positioning system 1008.

The ultrasonic transducer 1006 may also contain multiple elements for emitting ultrasound. A power supply which is not shown may control the amplitude and/or phase and/or frequency of alternating current electric power supplied to the elements of the ultrasonic transducer 1006. The dashed lines 1012 show the path of ultrasound from the ultrasonic transducer 1006. The ultrasound 1012 first passes through the fluid-filled chamber 1004. The ultrasound then passes through an ultrasound window 1014. After passing through the ultrasound window 1014 the ultrasound passes through an optional gel pad 1016 or a layer of ultrasound conductive gel which may be used to conduct ultrasound between the window 1014 and the subject 818. The ultrasound 1012 then enters the subject 818 and is focused into a focus 1018 or sonication point. There is a region 1020 which is a target zone. Through a combination of electronic and mechanical positioning of the focus 1018 the entire target zone 1020 can be heated. The target zone 1020 is within the imaging zone 808. The high-intensity focused ultrasound system 1002, the transceiver 816, and the magnetic field gradient coil power supply 812 are all connected to a hardware interface 828 of computer system 826.

The computer storage 834 is shown as additionally containing treatment plan data 1030 that has been received from an external computer, storage device, or from the user interface 832. The computer storage 834 is shown as further containing a thermal map 1032 that has been reconstructed from the magnetic resonance data 842. For instance the pulse sequence data 840 could contain instructions for acquiring thermal magnetic resonance data. The computer storage 834 is shown as further containing treatment system control commands 1034 which were generated using the thermal map 832 and the treatment plan data 1030. Alternatively the magnetic resonance image 844 could also be used. For instance the movement of the subject 818 could be tracked as well as making a thermal map of how the subject 818 is being heated inside.

The computer memory 836 is shown as additionally containing a second selection of plug-ins which contain additional algorithms for processing the magnetic resonance data 840 or magnetic resonance image 844 or thermal map 1032. The second selection of plug-ins 1040 uses data to generate the treatment system control commands 1034. The treatment system control commands 1034 enable the processor 830 to control the high-intensity focused ultrasound system 1002 via the hardware interface 828.

Figure 11:
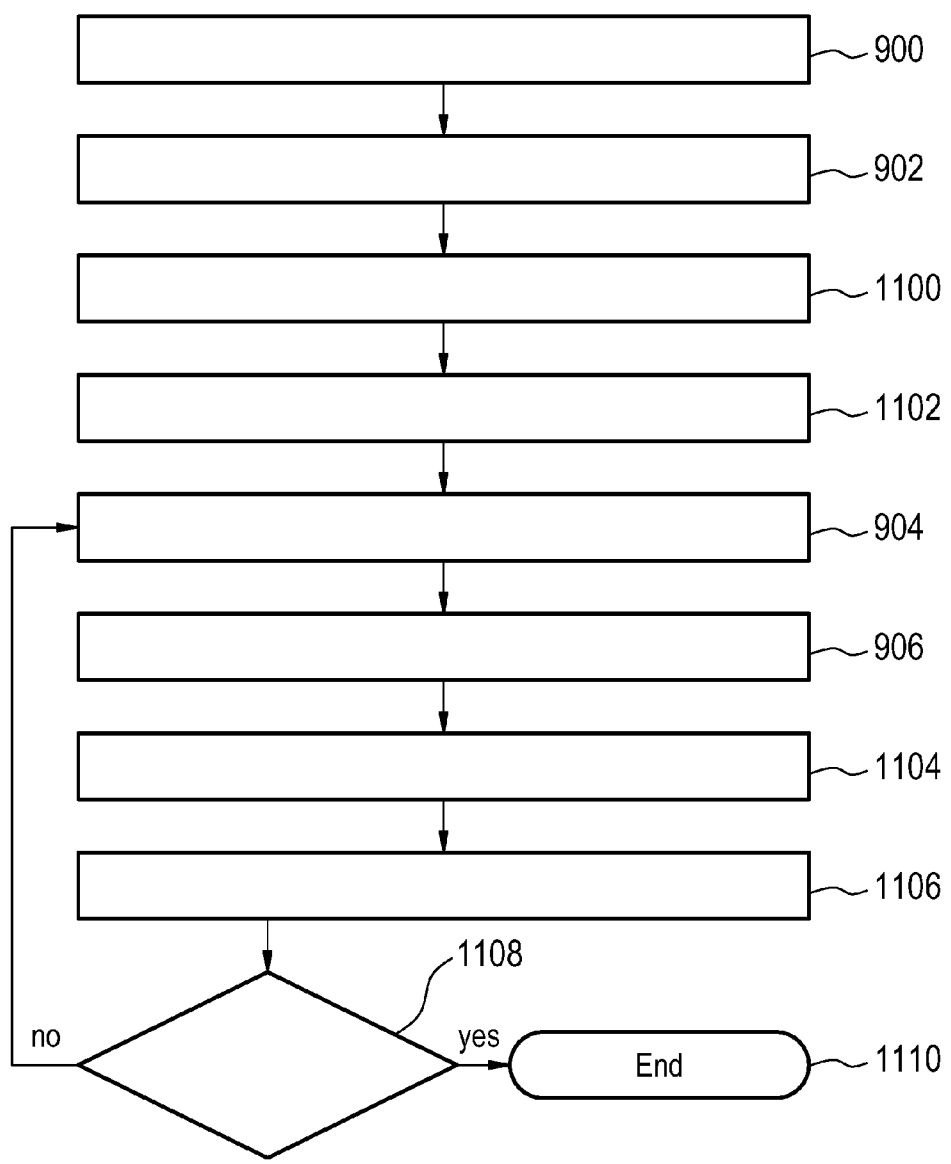
FIG. 11 shows a block diagram which illustrates a method of operating the medical instrument of FIG. 10.

FIG. 11 shows a flow diagram which illustrates a method of operating the medical instrument 1000 of FIG. 10. First step 900 as described in FIG. 9 is performed. Next step 902 as described for FIG. 9 is performed. Next step 1100 treatment plan data 1030 descriptive of commands for controlling the treatment system to direct energy at the target zone 1020 is received. Next in step 1102 a second selection of plug-ins 1040 operable for generating the treatment system control commands 1034 are loaded. Next step 904 as described for FIG. 9 is performed. Next step 906 as described for FIG. 9 is performed. Then next in step 1104 treatment system control commands 1034 are generated using the second selection of the plug-ins 1040 and the treatment plan data 1030 with the thermal map 1032 and/or the magnetic resonance image 844.

Next step 1106 is performed where the treatment system or in this case the high-intensity focused ultrasound system 1002 is controlled using the treatment system control commands 1034. The method then proceeds to a decision box 1108 where the question is is the treatment finished. If the treatment is finished then the method proceeds to step 1110 and the method described in FIG. 11 ends. If the answer is no the treatment is not yet finished, then the method goes back to step 904 and the steps 904, 906, 1104 and 1106 are repeated until the treatment is finished. These steps form a closed control loop and the first selection of plug-ins 858 and the second selection of plug-ins 1040 are used for controlling the high-intensity focused ultrasound system 1002 using the magnetic resonance data 842.

Figure 12:
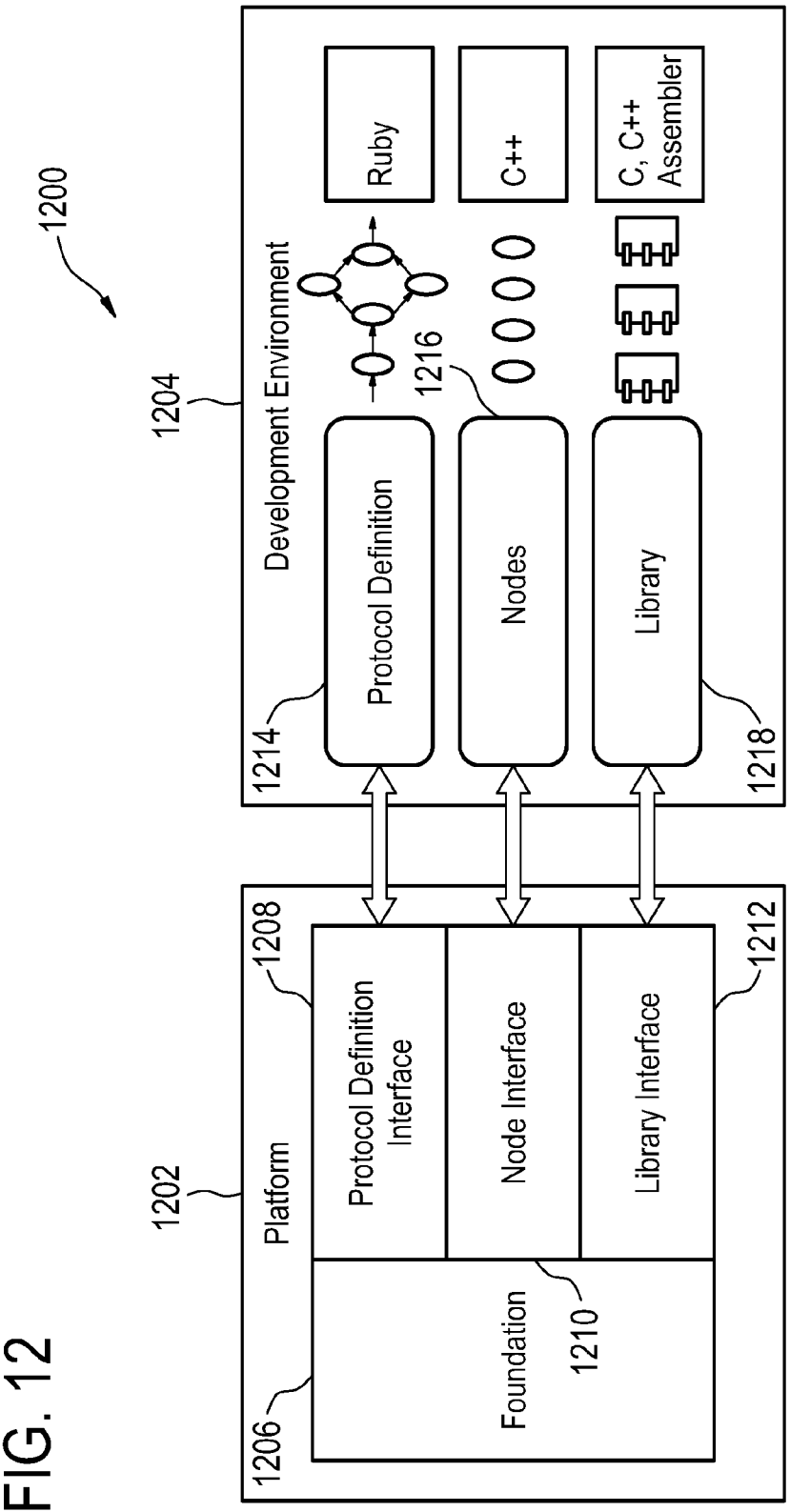
FIG. 12 illustrates a framework for implementing a magnetic resonance data processing system.

FIG. 12 illustrates a framework 1200 for implementing examples of a magnetic resonance data processing system. The framework 1200 comprises a platform 1202 and a development environment 1204. The platform 1202 comprises a foundation 1206. The foundation 1206 handles complex software engineering aspects such as threading, memory management, task scheduling, and other tasks. This is so that the reconstruction can make optimum use of the hardware. The platform 1202 also comprises a protocol definition interface which provides a Ruby infrastructure for instantiating and connecting the processing steps to each other in a reconstruction chain. Other languages than Ruby may be used also. The platform 1202 also contains a node interface 1210. The node interface enables data transfer across different steps in the reconstruction process by providing a completely modular, programmable interface. The node interface may also be referred to as the plug-in framework. The framework 1200 also comprises a library interface 1212. The library interface is a wrapper of a commercial or other libraries for performing numerical operations and exposes a simple, possibly intuitive interface for using the functions available in commercial libraries.

The development environment may contain modules which are adaptable and useful for clinical research and development. The development environment 1204 comprises a protocol definition 1214. This protocol definition 1214 may be a Ruby environment where the logic is used to create the nodes as implemented. Using a protocol definition script the behavior of the nodes can be configured and/or their execution changed. Reconstruction of images apply numerous independent processing steps in the raw data received from the scanner. In the proposed architecture, these processing steps have been designed as independent software units called nodes. The nodes may also be referred to as plug-ins. As a node therefore as a small independent software unit in the reconstruction chain which can be used to process the image data. The development environment 1204 further comprises a library module 1218. The library module may be wrapped over commercial libraries or other numerical libraries. Researchers can use the routines in any of these libraries or implement their own versions of the routines. The modules may also support GPU libraries. If a graphics card is available on the system the single processing routines like FFT convolution, and correlation or others can be executed on the graphics card itself, resulting in an enhanced performance.

Examples may provide a one-stop image reconstruction or data processing framework designed to decouple the entire software engineering (memory management, scheduling, execution time etc.) from the reconstruction logic. The framework not only insulates the researcher from the software engineering layers, but also provides a plug-and-play environment ready for introducing new algorithms.

Examples may provide a development environment with an absolutely modular design. In its transformation from raw data into the final image, the data from the scanner passes through a series of completely independent processing modules called Nodes. The object oriented, C++ interface containing the nodes performs many of the common reconstruction tasks and lends itself to reuse and reconfiguration.

Examples may simplify adding new algorithms or processing steps to existing reconstruction chains does not necessitate recompiling the complete software. The plug-and-play architecture of the platform ensures that introducing a new processing step only requires a simple modification in the Protocol Definition Script. The new algorithms developed can also be easily deployed in a clinical workflow.

The architecture defined in examples may be designed for efficient execution of algorithms on the hardware. It automatically parallelizes the execution of the algorithms to utilize all the processor/cores available in the system, ensuring the performance of the reconstruction matches that of the hardware. Support for commercial math/signal processing libraries With its Library module, the framework may provides a single programming interface over commercially available math and signal processing libraries such as IPP, MKL. Every math or signal processing routine can be individually configured at runtime without recompiling the software.

The proposed architecture ensures clear separation between the software engineering and the development (algorithm) environments.

The major building blocks of examples may comprise one or more of the following elements:

A. Platform—The Foundation handles complex software engineering aspects such as threading, memory management, task scheduling etc. so that the reconstruction can make optimum use of the hardware.

B. The Protocol Definition Interface provides the Ruby infrastructure for instantiating and connecting the processing steps to each other in a reconstruction chain. The Node Interface enables data transfer across different steps in the reconstruction process by providing a completely modular, programmable interface.

C. The Library Interface is a wrapper over commercial libraries and exposes a simple, intuitive interface for using the functions available in commercial libraries. The Development Environment contains those modules which are adaptable for clinical research and development.

D. Protocol Definition is a Ruby environment where the logic to identify and instantiate the Nodes is implemented. Using the Protocol Definition Script, the behavior of the Nodes can be configured and/or their order of execution changed.

Reconstruction involves applying numerous independent processing steps on the raw data received from the scanner. In the proposed architecture, these processing steps have been designed as independent software units called Nodes. A Node therefore, is the smallest independent software unit in the reconstruction chain which can process the image data.

E. The Library module is a wrapper over commercial libraries such as IPP, MKL, APL and NPP. Researchers can use the routines in any of these libraries or implement your own versions of the routines. The module also supports GPU libraries like NPP, CUDA etc. When the graphics card is available on the system, the signal processing routines like FFT, Convolution, and Correlation etc. can be executed on the graphics card itself, resulting in enhanced performance.

Figure 13:
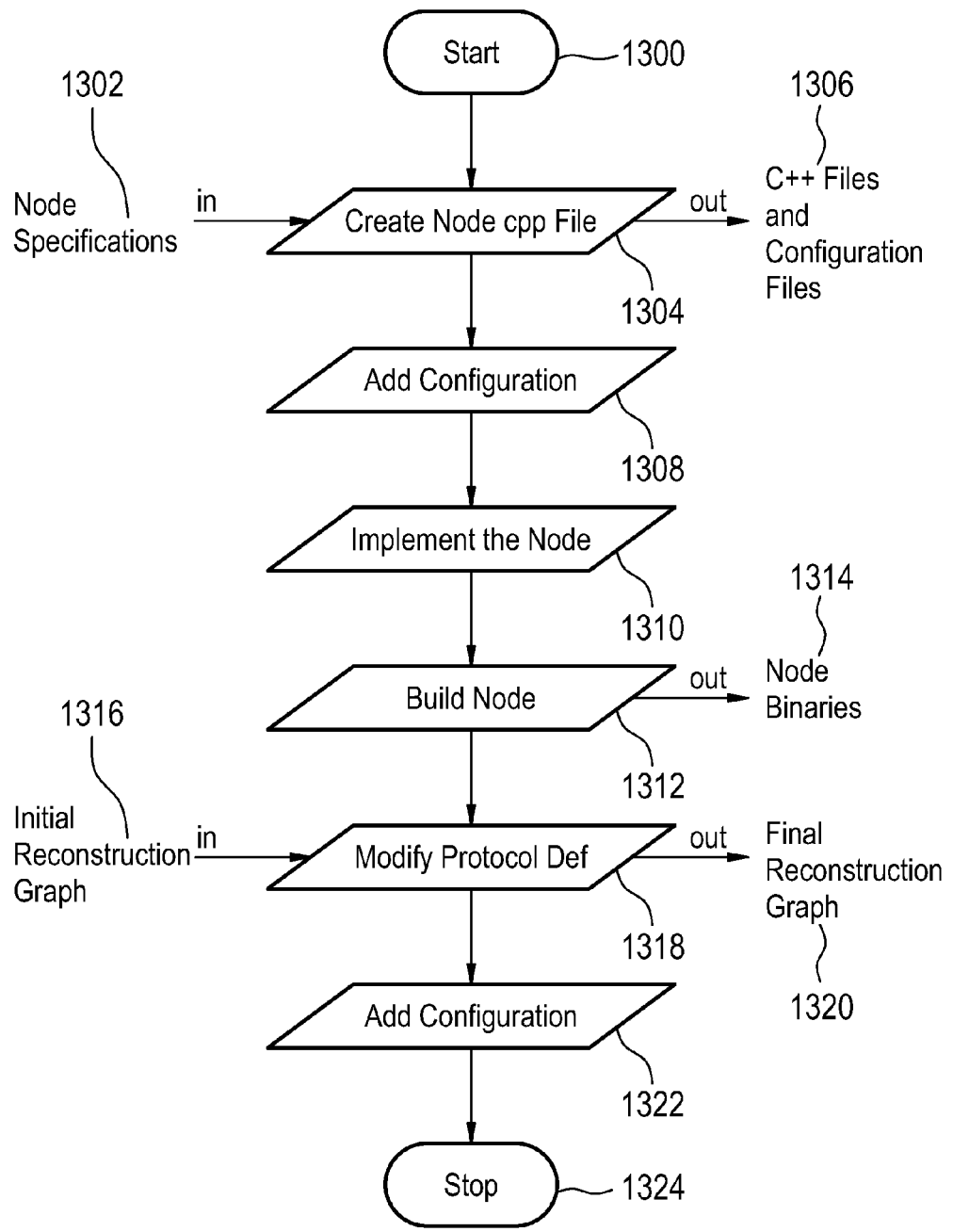
FIG. 13 shows a flowchart which illustrates a method of adding a new node or plug-in to the framework of FIG. 12.

FIG. 13 shows a flowchart which illustrates a method of adding a new node or plug-in to the system. The method starts in step 1300. In step 1302 a node specification is received and a node C++ file is created in step 1304. This results in C++ files and configuration files being created 1306. Next in step 1308 a configuration is added. Next in step 1310 the node or plug-in is implemented. Next in step 1312 the node is built. This results in the node binaries 1314 being outputted. In step 1316 an initial reconstruction graph is received. The initial reconstruction graph is equivalent to the protocol definition interface being executed. This is then used to modify the protocol definition 1318. This results in a final reconstruction graph 1320 being outputted. Next in step 1322 the particular configuration is added to the system and the method ends or stops in step 1324. Examples may also be used to control or drive additional hardware which can be used for therapy applications for example. Such a model would look as described in FIGS. 14 and 15.

FIG. 14 shows a reconstruction graph or the sequence is used to reconstruct a magnetic resonance image for a diagnostic magnetic resonance imaging system. First in step 1400 k-space data is received from the scanner or magnetic resonance imaging system. Next 1402 a correction is applied. Next in step 1404 a Fourier transform is performed. Next in step 1406 image production is performed or the image is reconstructed. Next in step 1408 the image is scaled. Finally in step 1410 the image is written to a database.

FIG. 15 shows how this chain may be modified so that the data may be used for controlling a magnetic resonance imaging system. After step 1408 the data is used to calculate a temperature map in step 1500. Next this is sent to a device drive 1502 which is used to control a high-intensity focused ultrasound system 1504. This adds support for magnetic resonance guided therapy. There could be certain maps needed to be computed and sent to a device driver 1502 which would then drive the external hardware 1504. The graph changes would only be an introduction of a new algorithm step or node for computation of the map in the triggers for the device driver with the appropriate data. In this architecture this would mean development of a new node copying the new node binaries to the reconstructor, modification of the graph, a couple of line changes and then addition of a hardware.

To add support for MR guided Therapy, where certain Maps need to be computed and sent to a device driver which would then drive the external hardware (outside of the reconstructor), the graph changes would be only an introduction of new algorithm step (Node) for computation of the Map and triggers the device driver with the appropriate data. In this new proposed architecture this would mean development of a new Node, copying of the new Node binaries to Reconstructor, modification of the graph (a couple of line changes) and then addition of hardware. The new modified graph would look like FIG. 15.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 1 image processing chain
2 raw image
3 processed image
4 algorithm 1
5 algorithm 2
6 algorithm 3
7 algorithm 4

8 implementation of magnetic resonance data processing application
9 algorithm 1
10 algorithm 2
11 algorithm 3
12 numerical library
13 configuration
14 thread pool
15 memory manager
16 receive data
17 manipulate data
18 apply algorithm
19 implementation of algorithm
20 send or return data
21 node
22 algorithm
23 node class
24 matlab node
25 configuration
26 matlab file
27 matlab file
28 library function
29 plug-in wrapper
30 numerical algorithm library
31 plug-in wrapper
32 numerical algorithm library
33 plug-in wrapper
34 numerical algorithm library
35 plug-in wrapper
36 numerical algorithm library
37 configuration file
38 k-space data or magnetic resonance data
40 input node
41 thread pool
42 reconstructor chain of plug-ins
43 reconstrutor
800 medical instrument
802 magnetic resonance imaging system
804 magnet
806 bore of magnet
808 imaging zone
810 magnetic field gradient coils
812 magnetic field gradient coil power supply
814 radio-frequency coil
816 transceiver
818 subject
820 subject support
826 computer system
828 hardware interface
830 processor
832 user interface
834 computer storage
836 computer memory
840 pulse sequence data
842 magnetic resonance data
844 magnetic resonance image
850 control module
852 magnetic resonance data processing application
854 numerical library
856 plug in wrapper library
858 first selection of plug-ins
860 protocol definition interface
900 execute the magnetic resonance data processing application thereby providing the plug-in framework
902 execute the protocol definition interface to load a first selection of the plug-ins into the plug-in framework;
904 acquire the magnetic resonance data by using the pulse sequence data to control the magnetic resonance imaging system
906 reconstruct a magnetic resonance image from the magnetic resonance data using the first selection of the plug-ins
1000 medical instrument
1002 high intensity focused ultrasound system
1004 fluid filled chamber
1006 ultrasonic transducer
1008 mechanical positioning system
1010 actuator
1012 path of ultrasound
1014 ultrasound window
1016 gel pad
1018 focus
1020 target zone
1030 treatment plan data
1032 thermal map
1034 treatment system control commands
1040 second selection of plug-ins
1100 receive treatment plan data descriptive of commands for controlling the treatment system to direct energy at the target zone
1102 load a second selection of the plug-ins operable for generating treatment system control commands using the magnetic resonance image and the treatment plan data
1104 generate the treatment system control commands using the second selection of the plug-ins
1106 control the treatment system using the treatment system control commands
1200 framework
1202 platform
1204 development environment
1206 foundation
1208 protocol definition interface
1210 node interface
1212 library interface
1214 protocol definition
1216 nodes or plug-ins
1218 library
1300 start
1302 node specification input
1304 create node cpp file
1306 cpp files and configuration files output
1308 add configuration
1310 implementing the node
1312 build node
1314 output node binaries
1316 input initial reconstruction graph
1318 modify protocol definitions
1320 output final reconstruction graph
1322 add configuration
1324 stop
1400 receive k-space data
1402 apply correction
1404 Fourier transform
1406 image production
1408 scale
1410 write to database
1500 calculate temperature map
1502 device driver
1504 external treatment system

The invention claimed is:
1. A computer program product comprising machine executable instructions for execution by at least one proces- sor controlling a medical instrument; wherein the medical instrument comprises a magnetic resonance imaging system for acquiring magnetic resonance data from an imaging zone; wherein the medical instrument further comprises a memory containing: a magnetic resonance data processing application pulse sequence data, at least one numerical algorithm library, a plug-in wrapper library configured for providing the least one numerical algorithm library as plug-ins, and a protocol definition interface; wherein the at least one numerical algorithm library comprises machine executable code for performing at least one numerical algorithm; wherein the magnetic resonance data processing application is configured for implementing a plug-in framework for numerical processing of the magnetic resonance data; wherein the protocol definition interface is configured for controlling the loading of the plug-ins and the execution order of the plug-ins; and wherein execution of the instruction cause the at least one processor to:

execute the magnetic resonance data processing application thereby providing the plug-in framework, execute the protocol definition interface to load a first selection of the plug-ins into the plug-in framework, acquire the magnetic resonance data by using the pulse sequence data to control the magnetic resonance imaging system, and reconstruct a magnetic resonance image from the magnetic resonance data using the first selection of the plug-ins.

2. The computer program product of claim 1, wherein the medical instrument further comprises a treatment system for directing energy at a target zone within the imaging zone, wherein execution of the instructions further cause the processor to receive treatment plan data descriptive of commands for controlling the treatment system to direct energy at the target zone, wherein execution of the protocol definition interface further loads a second selection of the plug-ins operable for generating treatment system control commands using the magnetic resonance image and the treatment plan data, wherein execution of the instructions further cause the at least one processor to repeatedly: acquire the magnetic resonance data and reconstruct the magnetic resonance image using the first selection of the plug-ins, generate the treatment system control commands using the second selection of the plug-ins, and control the treatment system using the treatment system control commands.

3. A method of operating a medical instrument comprising a magnetic resonance imaging system for acquiring magnetic resonance data from an imaging zone; wherein the medical instrument further comprises a memory containing: a magnetic resonance data processing application pulse, sequence data, at least one numerical algorithm library, a plug-in wrapper library configured for providing the least one numerical algorithm library as plug-ins, and a protocol definition interface; wherein the at least one numerical algorithm library comprises machine executable code for performing at least one numerical algorithm; wherein the magnetic resonance data processing application is configured for implementing a plug-in framework for numerical processing of the magnetic resonance data; wherein the protocol definition interface is configured for controlling the loading of the plug-ins and the execution order of the plug-ins; and wherein the method comprises the steps of: executing the magnetic resonance data processing application thereby providing the plug-in framework, executing the protocol definition interface to load a first selection of the plug-ins into the plug-in framework, acquiring the magnetic resonance data by using the pulse sequence data to control the magnetic resonance imaging system, and reconstructing a magnetic resonance image from the magnetic resonance data using the first selection of the plug-ins.

4. The method of claim 3, wherein the medical instrument further comprises a treatment system for directing energy at a target zone; within the imaging zone, wherein the method further comprises receiving treatment plan data descriptive of commands for controlling the treatment system to direct energy at the target zone, using the protocol definition interface to further load a second selection of the plug-ins operable for generating treatment system control commands using the magnetic resonance image and the treatment plan data, wherein the method further comprises the steps of repeatedly:

acquiring the magnetic resonance data and reconstructing the magnetic resonance image using the first selection of the plug-ins;

generating the treatment system control commands using the second selection of the plug-ins, and controlling the treatment system using the treatment system control commands.

\* \* \* \* \*